United States Patent
Clough et al.

(10) Patent No.: US 9,110,022 B2
(45) Date of Patent: Aug. 18, 2015

(54) ACOUSTIC METHODS AND SYSTEMS FOR DETECTING TERAHERTZ RADIATION

(75) Inventors: Benjamin Clough, Arlington, VA (US); Jingle Liu, Troy, NY (US); Xi-Cheng Zhang, Melrose, NY (US)

(73) Assignee: RENSSELAER POLYTECHNIC INSTITUTE, Troy, NY (US)

(*) Notice: Subject to any disclaimer, the term of this patent is extended or adjusted under 35 U.S.C. 154(b) by 351 days.

(21) Appl. No.: 13/643,871

(22) PCT Filed: Apr. 29, 2011

(86) PCT No.: PCT/US2011/034466
§ 371 (c)(1),
(2), (4) Date: Feb. 14, 2013

(87) PCT Pub. No.: WO2012/012005
PCT Pub. Date: Jan. 26, 2012

(65) Prior Publication Data
US 2013/0153790 A1 Jun. 20, 2013

Related U.S. Application Data

(60) Provisional application No. 61/343,476, filed on Apr. 29, 2010.

(51) Int. Cl.
*G01N 21/63* (2006.01)
*G01N 21/3504* (2014.01)
*G01N 21/3581* (2014.01)

(52) U.S. Cl.
CPC ............ *G01N 21/63* (2013.01); *G01N 21/3504* (2013.01); *G01N 21/3581* (2013.01)

(58) Field of Classification Search
CPC G01N 21/3581; G01N 21/636; G01N 21/718
See application file for complete search history.

(56) References Cited

U.S. PATENT DOCUMENTS

| | | | |
|---|---|---|---|
| 7,087,902 B2 * | 8/2006 | Wang et al. | 250/341.1 |
| 7,531,802 B2 | 5/2009 | Zhang et al. | |
| 2004/0011967 A1 * | 1/2004 | Nutting et al. | 250/492.1 |
| 2007/0145276 A1 * | 6/2007 | Zhang et al. | 250/341.1 |
| 2008/0203306 A1 | 8/2008 | Zhang et al. | |
| 2009/0173159 A1 | 7/2009 | Reed et al. | |

OTHER PUBLICATIONS

Van Tilborg, Jeroen, Coherent terahertz radiation from laser-wakefield-accelerated electron beams, Technische Universiteit Eindhoven, 2006, pp. 1-147.
International Search Report for PCT/US2011/034466 dated Dec. 28, 2011.

* cited by examiner

*Primary Examiner* — David J Makiya
*Assistant Examiner* — Kenneth J Malkowski
(74) *Attorney, Agent, or Firm* — Heslin Rothenberg Farley & Mesiti P.C.

(57) ABSTRACT

Methods and systems for detecting radiation for example, terahertz radiation, with the aid of acoustic signal generation and detection include: directing an optical beam into a volume of gas; ionizing at least a portion of the volume of gas with the optical beam to produce a plasma; and detecting an acoustic signal produced from an interaction of a radiation wave with the plasma. The methods and systems are particularly adapted for remote detection of chemicals, biological substances, and explosives, among others. The capability of the methods and systems can be enhanced by employing multi-color laser excitation to produce the plasma and varying the time delay between the multi-color pulses.

10 Claims, 10 Drawing Sheets

US 9,110,022 B2

ACOUSTIC METHODS AND SYSTEMS FOR DETECTING TERAHERTZ RADIATION

CROSS-REFERENCE TO RELATED APPLICATION

This application is a national stare filing under section 371 of international Application No. PCT/US2011/034466 filed on Apr. 29, 2011, and published in English on Jan. 26, 2012 as WO 2012/012005 A1 and claims priority from U.S. Provisional Patent Application 61/343,476, filed on Apr. 29, 2010, the entire disclosure of these applications being hereby incorporated herein by reference.

This application is related to pending U.S. patent application Ser. No. 13/095,276 filed on Apr. 27, 2011, the disclosure of which is hereby incorporated herein by reference.

This application is also related to pending U.S. patent application Ser. No. 13/097,866 filed on Apr. 29, 2011, the entire disclosure of which is hereby incorporated herein by reference.

STATE AND FEDERAL FUNDED RESEARCH

The invention described herein was made with U.S. Government support under Contract Number 2008-ST-061-ED001 awarded by the Department of Homeland Security (DHS), under Contract Number HDTRA1-09-1-0040 awarded by the Defense Threat Reduction Agency (DTRA), under grant No. 0333314 awarded by the National Science Foundation (NSF). The U.S. Government has certain rights to this invention.

BACKGROUND OF THE INVENTION

1. Field of the Invention

The present invention relates, generally, methods and systems for detecting radiation, for example, terahertz radiation. In particular, the prevention comprises methods and systems for detecting terahertz radiation by detecting the acoustic emissions from the interaction of terahertz radiation with a plasma.

2. Description of Related Art

The work of Zhang, et al. as exemplified by U.S. Pat. Nos. 7,531,802; 7,595,491; 7,652,253; and 7,808,636, among others, underscores the unique potential for terahertz (THz) wave sensing and detection to provide marked improvements in the detection and analyses of materials, in particular, materials harmful to humans, such as, explosives. As is known in the art, THz electromagnetic radiation lies in the electromagnetic spectrum between infrared radiation waves and microwaves.

Although THz-based detecting techniques continues to excel in spectroscopic studies, such as, in-situ and non-destructive evaluation of materials, the ability to conduct such measurements from a significant remote or "stand-off" distance has remained elusive. This is primarily due to inherent THz absorption by atmospheric water vapor. Various THz detection methods have been introduced; however, methods for true remote coherent detection remain to be developed. Recently, the ability to remotely generate THz using optical wavelengths focused at a distance has shown promise in reducing THz free space interaction by a factor of two. Nonetheless, this does not entirely solve the problem since THz attenuation in air can be as high as 100 decibels/kilometer. Among various THz detection methods, it has been demonstrated that air may be used as a coherent THz detector, and applying a modulated electric field to the nonlinear optical interaction between a THz pulse and an 800 nm optical pulse can greatly enhance the detected coherent information. However, methods for true remote coherent detection without the need for on-site electrodes or cabling remain to be developed.

Laser-induced plasma continues to gain interest because of its increasing number of scientific and technological applications in photo-ionization, high-harmonic generation, laser-induced breakdown spectroscopy, spark-induced breakdown spectroscopy, and the generation and detection of broadband terahertz (THz) pulses. Since the advent of millijoule, femtosecond pulsed lasers, laser-induced plasma has been employed to study the interaction between light and matter and reveal ultrafast dynamics of solids, liquids, and gases. However, the respective fields of THz photonics and photo-acoustics have, for the most part, remained non-overlapping. Laser-induced plasma acoustic dynamics under the influence of single-cycle electromagnetic radiation and its underlying physical mechanism currently remain unexplored.

While some work has been conducted to send THz waves to a remote distances directly, these methods are limited by the extreme absorption of THz by atmospheric water vapor and therefore cannot be extended beyond a few meters, that is, distances which still make the, for example, hazard under study a potential threat to the operator. Aspects of the present invention take the advantageous abilities of THz radiation for non-invasive imaging and chemical identification and provide systems and method for separating the potentially hazardous item from the operator by encoding the THz information into the acoustic waves emitted from a laser-induced plasma, for example, which can be formed at a remote location.

Aspects of the present invention provide methods and systems that bridge the unintentional gap between THz photonics and photo-acoustics and introduce new tools to the arsenal for remote detection, for example, for biological, physical, and defense-based applications, among others.

SUMMARY OF ASPECTS OF THE INVENTION

Aspects of the present invention pertain to a recently uncovered phenomenon regarding the enhanced acoustic emission from laser-induced plasma under the influence of a THz pulse, for example, a single-cycle THz wave pulse. The present invention employs the evolutionary process in which these acoustic waves produced from the interaction between THz electromagnetic radiation and a plasma, for example, a laser-induced plasma, can be detected and analyzed. When, for example, either a single-color (for example, 800 nanometer [nm]), or a dual-color (for example, 800 nm and 400 nm) femtosecond laser pulse, is focused in air, an acoustic pulse is produced, for example, a broadband acoustic pulse. That is, according to aspects of the invention, under the influence of THz radiation, an enhancement of the sound pressure is produced, in particular, the enhancement of the sound pressure is produced in the far field after relaxation of an initial shock wave front. According to aspects of the present invention, the enhanced sound pressure, or acoustic signal, produced by the interaction of THz with a plasma provides a vehicle for detecting variations in the plasma, for example, variations in the plasma under the influence of incident THz radiation.

One embodiment of the present invention is a method of detecting radiation comprising or including the steps of directing an optical beam into a volume of gas; ionizing at least a portion of the volume of gas with the optical beam to produce a plasma; and detecting an acoustic signal produced from an interaction of a radiation wave with the plasma. In one aspect, the radiation wave may be microwaves, infrared light, visible light, ultraviolet light, x-rays (soft and hard), gamma rays, or radio waves; however, in one aspect, the radiation wave comprises terahertz waves. The acoustic signal for this or any other embodiment or aspect disclosed herein may be an enhanced acoustic signal, for example, an acoustic signal that varies, for instance, is increased in amplitude, from an acoustic signal present without the presence of the radiation wave. The acoustic signal may be an infrasonic, a sonic, or an ultrasonic acoustic signal, for example, an omni-directional sonic or ultrasonic signal. In one aspect, the ionizing of the volume of the gas comprises at least one of single-color pulse excitation and multi-color pulse excitation, for example, dual-color pulse excitation. In another aspect, the method comprises a remote sensing method, for example, where an operator may be several meters, for example, at least 1 meter from the target, at least 3 meters from the target, or at least 10 meters from the target.

Another embodiment of the invention is a method of detecting a target, the method comprising or including the steps of directing a first optical beam into a first volume of gas; ionizing at least a portion of the first volume of gas with the first optical beam to produce an emitter plasma and to emit terahertz radiation directed toward a target; directing a second optical beam into a second volume of gas; ionizing at least a portion of the second volume of gas with the second optical beam to produce a sensor plasma; and detecting an acoustic signal produced from an interaction of an incident terahertz wave with the sensor plasma, the incident terahertz wave produced by an interaction of the terahertz radiation with the target. In another aspect, the first optical beam and/or the second optical beam may be a dual-color laser pulse having a first pulse at a first frequency and a second pulse at a second frequency different from the first frequency, and wherein the first pulse and the second pulse are temporally separated by a time delay. The time delay may be varied.

A further embodiment of the invention is a system for detecting radiation comprising or including an optical beam directed into a volume of a gas wherein at least a portion of the volume of the gas is ionized and a plasma is produced; and a detector for detecting an acoustic signal emitted from an interaction of an incident radiation wave with the plasma. The incident radiation wave may be microwaves, infrared light, visible light, ultraviolet light, x-rays (soft and hard), gamma rays, or radio waves; however, it is typically terahertz waves. In one aspect, ionizing the volume of the gas may be practiced by single-color pulse excitation and multi-color pulse excitation, for example, dual-color pulse excitation ionization. In another aspect, dual-color pulse excitation ionization may be provided by a first pulse at a first frequency and a second pulse at a second frequency different from the first frequency, and wherein the first pulse and the second pulse are temporally separated by a time delay. Means for varying the time delay may be provided, for example, a phase compensator may be used.

In one aspect, the optical beam may be a first optical beam and the volume of gas may be first volume of gas, wherein the system may further include a second optical beam directed into a second volume of gas wherein at least a portion of the second volume of the gas is ionized and a terahertz wave is produced; and wherein the terahertz wave comprises the source of incident radiation wave. In one aspect, the incident radiation wave may be a terahertz wave resulting from the interaction of the terahertz wave from the second volume of gas and a target.

Details of these aspects of the invention, as well as further aspects of the invention, will become more readily apparent upon review of the following drawings and the accompanying claims.

BRIEF DESCRIPTION OF THE FIGURES

The subject matter that is regarded as the invention is particularly pointed out and distinctly claimed in the claims at the conclusion of the specification. The foregoing and other objects, features, and advantages of the invention will be readily understood from the following detailed description of aspects of the invention taken in conjunction with the accompanying drawings in which:

DETAILED DESCRIPTION OF FIGURES

Figure 1:
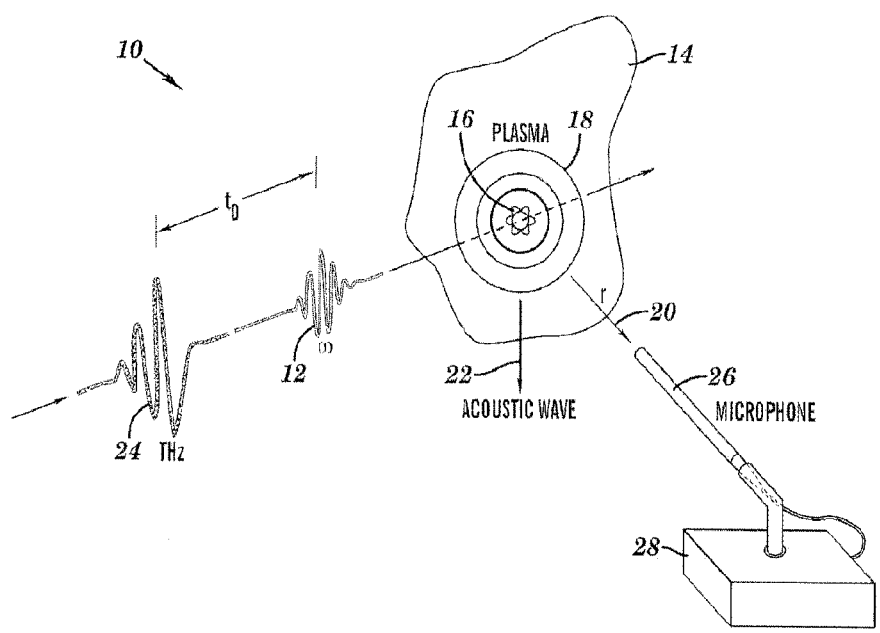
FIG. 1 is a schematic diagram of a detection method and system according to one aspect of the invention.

The details and scope of the aspects of the present invention can best be understood upon review of the attached figures and their following descriptions. FIG. 1 is schematic diagram of a detection method and system 10 according to one aspect of the invention. As shown in FIG. 1, by directing, for example, focusing, an optical beam 12, for example, a laser beam, into a volume of gas 14, for example, air, and ionizing at least a portion of the volume of gas 14 with the optical beam 12 a plasma 16 can be formed, for example, a plasma that can be used to sense radiation, for example, a "sensor plasma." The total laser intensity at the focus of optical beam 12 in volume of gas 14 may typically be between about $10^{13}$ to $10^{14}$ Watts per square centimeter [W/cm$^2$].

Under illumination by such an optical beam, for example, an intense femtosecond [fs] laser pulse, the molecules in at lease a portion of the volume of gas 14 are excited and then ionized by releasing one or more free electrons through multi-photon ionization or tunneling ionization. It is conjectured that after rejection from the atoms or molecules during the leading part of the laser pulse, the electrons are accelerated by the rest of the laser pulse and drift away from their parent ions. In this intense laser field excitation, the electron temperature is usually much higher than the temperature of the neutral particles, for example, mostly molecules in air and ions, having masses that are generally thousands of times larger than electron mass. Before the electron-ion recombination, these "hot" electrons collide with the neighboring "cold" molecules and transfer some portion of their kinetic energy to the molecules through the inelastic electron-molecule collision in the following nanoseconds. The subsequent translational motion of the molecules gives rise to the creation of a shock wave which then relaxes into an acoustic wave, for example, acoustic signal 18 shown in FIG. 1.

According to aspects of the invention, the acoustic signal 18, for example, a sound wave or an air pressure wave, is produced during the generation of the plasma 16. The acoustic signal 18 may be an acoustic pulse, for example, a broadband acoustic pulse. It has been found that the propagation of the acoustic signal 18 is typically multidirectional, that is, emanating in substantially all directions in three-dimensional space. For the sake of illustration, acoustic signal 18 may be represented by vectors 20 and 22 shown in FIG. 1.

The inventors have discovered that the characteristics of the acoustic signal 18 can be affected by the interaction of the plasma 16 with a radiation wave 24, for example, a THz radiation wave. According to aspects of the invention, by detecting the acoustic signal 18 produced from an interaction of a radiation wave 24 with the plasma 16 at least one, but typically, multiple, characteristics of the radiation wave 24 can be detected. As shown, one method of detecting acoustic signals 18 can be by using a microphone 26, for example, a microphone 26 coupled to a receiver 28, though any type of acoustic wave detector which is adapted to detect acoustic waves 18 may be used for microphone 26. As is conventional, a microphone 26 may generate an electrical signal representative of acoustic signal 18 that can be transmitted and received by a receiver 28. Acoustic detector or a microphone 26 may be within millimeters of plasma 18 or within several meters of plasma 18, for example, 5 meters or 10 meters away from plasma 18, or even 50 meters away from plasma 18. Receiver 28 may include an oscilloscope or a lock-in amplifier (LIA) for the measurement, characterization, and display of acoustic signal 18, for example, a discrete frequency.

In FIG. 1 the radiation wave 24 is identified as a THz wave; however, according to aspects of the invention, the radiation wave 24 may be any form of electromagnetic radiation, for example, microwaves, infrared waves, visible light, ultraviolet (UV) light extreme ultraviolet (EUV) light, x-rays, gamma rays, and radio waves.

In one aspect, radiation wave 24 may be a single-cycle THz pulse with peak field of approximately 100 kiloVolts per centimeter [kV/cm], for example, a pulse generated using the tilted pulse front optical rectification technique in $LiNbO_3$. As shown in FIG. 1, in one aspect of the invention, the optical beam 12 may comprise a laser pulse, for example, a femtosecond laser pulse, having a wavelength $\omega$, for example, of about 800 nanometer [nm], that is, the optical beam 12 may have a "single color." As used here and throughout this disclosure, frequencies may be specified in nanometers (nm), where the specified frequency corresponds to radiation having about the given wavelength in nanometers.

As also shown in FIG. 1, radiation wave 24, for example, a THz wave, may be directed in the same path or direction or along substantially the same path or direction as optical beam 12, for example, co-incident with optical beam 12. However, according to aspects of the present invention, radiation wave 24 may be directed in any direction, for example, radiation beam 24 may be directed onto or into to plasma 16 from any direction, that is, radiation beam 24 may be omni-directional, and have little or no relationship to the direction or path of optical beam 12. In one aspect, the single-cycle THz pulse 24 may be spatially overlapped with optical beam 12, for example, overlapped with an 800 nm, 65 fs, 110 mJ pulse energy, and 1 kHz repetition rate laser pulse. The "65 fs" specification means that the full width half magnitude of the laser pulse is around 65 fs.

As also shown in FIG. 1, in one aspect, there may be a temporal relationship between optical beam 12 and radiation wave 24, for example, the timing of impact of optical beam 12 upon a portion of the volume of gas 14 and the impact of radiation wave 24 on the portion of the volume of gas 14 may be separated by a time delay $t_D$. Time delay $t_D$ may be positive, negative, or substantially zero, and, according to an aspect of the invention, may be variable or controllable. According to aspects of the invention, a negative time delay, $t_D$, represents a condition in which the plasma generating optical beam 12 leads the radiation wave 24, that is, optical beam 12 impacts or is present within the portion of the volume of gas 14 before the radiation wave 24. The inventors have found that when the time delay $t_D$ is negative (that is, optical beam pulse 12 precedes the radiation wave 24, for example, a THz pulse), the acoustic pressure wave 18 is observed to be enhanced by the radiation wave field, for example, the THz radiation field.

Figure 2:
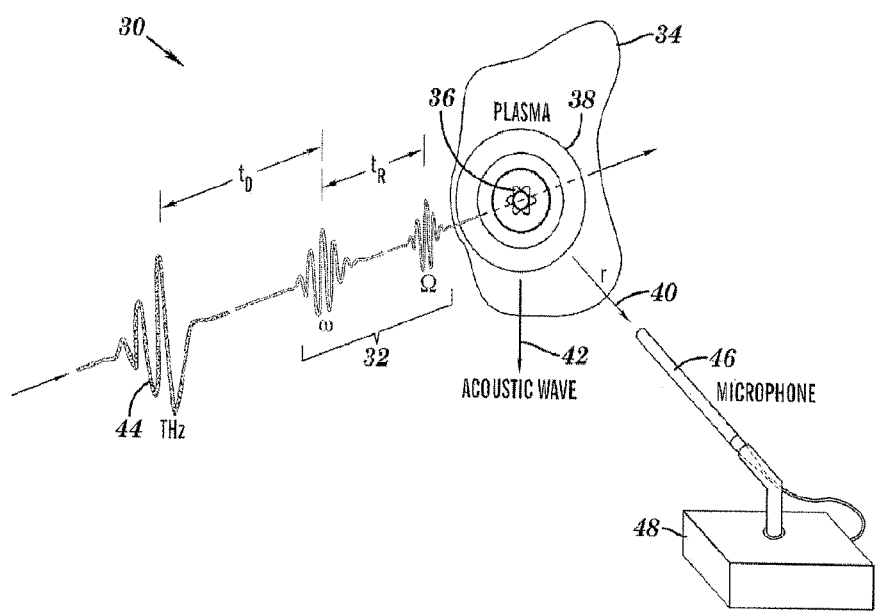
FIG. 2 is a schematic diagram of detection method and system according to another aspect of the invention.

FIG. 2 is a schematic diagram of detection method and system 30 according to another aspect of the invention. In a fashion similar to system 10 shown in FIG. 1, method and system 30 also includes directing, for example, focusing, an optical beam 32, for example, a laser beam, into a volume of gas 34, for example, air, and ionizing at least a portion of the volume of gas 34 with the optical beam 32 to form a plasma 36, for example, a "sensor plasma." According to aspects of the invention, an acoustic signal 38, for example, a sound wave or an air pressure wave, is produced during the generation of the plasma 36. According to one aspect of the invention, the acoustic signal 38 like acoustic signal 18 may be an acoustic pulse, for example, a broadband acoustic pulse, may typically be multidirectional, and may be represented by vectors 40 and 42 shown in FIG. 2. Again, as in system 10, the characteristics of the plasma 36 can be affected by the interaction of plasma 36 with a radiation wave 44, for example, a THz radiation wave. By detecting the acoustic signal 38 produced from the interaction of the radiation wave 44 with the plasma 36 at least one, but typically, multiple, characteristics of the radiation wave 44 can be detected. Again, as in system 10, one method of detecting acoustic signal 38 can be by using a microphone 46, for example, a microphone 46 coupled to a receiver 48, though any type of acoustic wave detector may be used. In FIG. 2 the radiation wave 44 is identified as a THz wave; however, according to aspects of the invention, the radiation wave 44 may be any form of electromagnetic radiation, for example, microwaves, infrared waves, visible light, ultraviolet (UV) light extreme ultraviolet (EUV) light, x-rays, gamma rays, and radio waves.

As shown in FIG. 2, in this aspect of the invention, the optical beam 32 may comprise a laser, for example, a femtosecond laser pulse, having two or more wavelengths $\omega$ and $\Omega$. For instance, $\Omega$ may be a harmonic of $\omega$, for instance, $\Omega$ may be a second harmonic, where $\Omega \approx 2\omega$. For example, $\omega$ may be about 800 nm and $\Omega$ may be about 400 nm (that is, twice the frequency, but half the wavelength). That is, in the system 30 shown in FIG. 2, the optical beam 32 may be "multi-colored," in particular, "dual colored."

As also shown in FIG. 2, radiation wave 44, for example, a THz wave, may be directed in the same direction as optical beam 32, for example, co-incident with optical beam 32. However, according to aspects of the present invention, radiation wave 44 may be directed in any direction, for example, radiation wave 44 may be directed onto plasma 36 from any direction, that is, dual-color radiation beam 44 may be omni-directional, and have little or no relationship to the direction of optical beam 32. As also shown in FIG. 2, in one aspect, there may be a temporal relationship between optical beam 32 and radiation wave 44 and also between the two or more pulses having wavelengths ω and Ω of optical beam 32. For example, the timing of impact of optical beam 32 upon a portion of the volume of gas 34 and the impact of radiation wave 44 on the portion of the volume of gas 44 may be separated by a time delay $t_D$, as in system 10 of FIG. 1. However, in the dual-color system 30 of FIG. 2, there may also be a time delay $t_R$ between the two pulses at wavelengths of optical beam 32. Time delays $t_D$ and $t_R$ may be positive, negative, or substantially zero, and, according to an aspect of the invention, each time delay may be variable or controllable, for example, by use of a phase compensator. One phase compensator that may be used is described by Dai, et al. "In-line phase compensator for intense THz generation in selected gases," Infrared, Millimeter, and Terahertz Waves, 2009. IRMMW-THz 2009, 34th International Conference on 21-25 Sep. 2009, which is incorporated by reference herein in its entirety. According to aspects of the invention, a positive time delay, $t_D$, represents a condition in which the plasma generating optical beam 32 leads the radiation wave 44, that is, optical beam 32 impacts the portion of the volume of gas 34 before the radiation wave 44.

According to aspects of the present invention, by employing multi-color laser excitation, for example, dual-color laser excitation, for optical beam 32, the "net electron drift" in the plasma 36 created by optical beam 32 can be manipulated.

Figure 3:
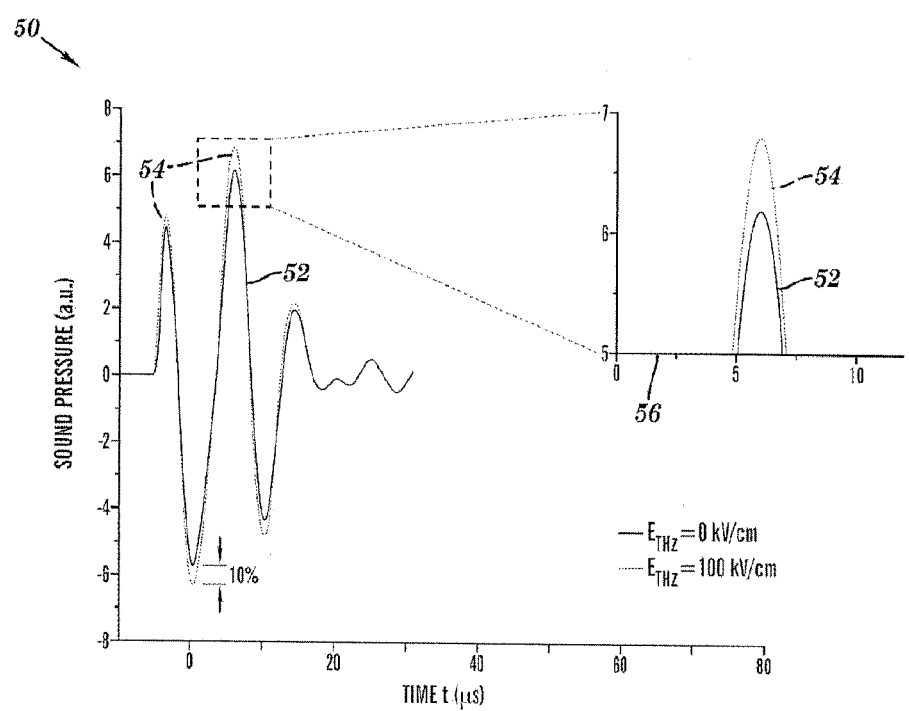
FIG. 3 is a graphical illustration of measured acoustic waveforms that can be produced with the systems shown in FIGS. 1 and 2.

FIG. 3 is a graphical representation 50 of measured acoustic waveforms that can be produced with the systems shown in FIGS. 1 and 2. FIG. 3 illustrates single photo-acoustic waveforms 52 and 54 measured at a 5 millimeter [mm] distance from a plasma produced when a 110 microjoule [μJ], 65 femtosecond [fs], 800 nm laser pulses (that is, a single-color optical signal 12 in FIG. 1) is focused into air. The waveforms 52 and 54 may be produced by the single-color system 10 shown in FIG. 1. Waveform 52, that is, the black-sold waveform, corresponds to the acoustic signal (or "sound pressure") produced when substantially no radiation wave, that is, no radiation wave 24 of FIG. 1, is present in or about the plasma, for example, plasma 16 of FIG. 1. Waveform 54, that is, the red-dashed waveform, corresponds to the acoustic signal produced when a THz wave of about 100 kiloVolts [kV] per centimeter [cm], that is, radiation wave 24 of FIG. 1, is present in or about the plasma, for example, plasma 16 of FIG. 1. As shown in FIG. 3, especially in inset 56, in this aspect of the invention, the presence of the 100 kV per cm THz radiation enhances the amplitude of waveform 54 compared to the amplitude of waveform 52 with no such THz radiation present. According to aspects of the invention, the enhancement in the amplitude of the sound pressure at a given time may be at least about 5%, or at least about 10%, as shown in FIG. 3. Under appropriate conditions, it is conceived that the enhanced sound pressure may be enhanced at least about 15%, or at least about 20%, and even at least about 25%, or higher, than when little or no radiation wave is present. Accordingly, in aspects of the invention, the methods and systems disclosed herein may be useful in detecting the presence of radiation waves, for example, THz radiation waves, by detecting enhancements or variations in the acoustic signal detected, for example, by an acoustic signal detector.

Figure 4:
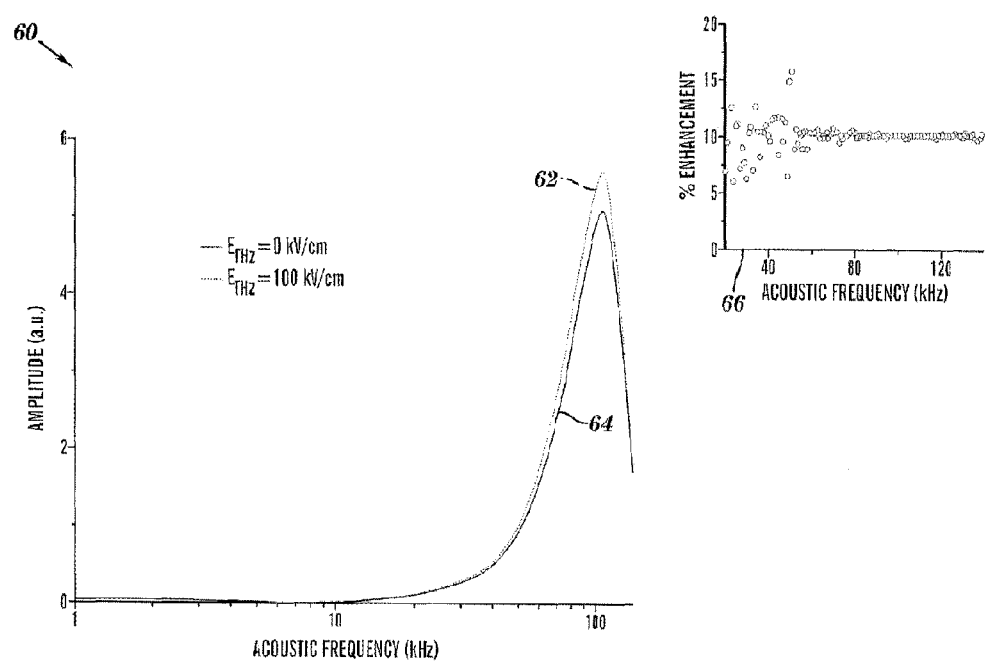
FIG. 4 is graphical illustration of the pressure enhancement achievable according to aspects of the invention in the frequency domain.

FIG. 4 is graphical representation 60 of the pressure enhancement achievable according to aspects of the invention in the frequency domain. FIG. 4 illustrates single photo-acoustic frequency domain waveforms 62 and 64 after Fourier transformation of the single-pulse temporal, that is, time domain, waveforms 52 and 54 shown in FIG. 3. That is, frequency domain waveforms 62 and 64 were measured at a 5 mm distance from a plasma produced when a 110 mJ, 65 fs, 800 nm laser pulses are focused into air. Frequency domain waveform 64, that is, the black-sold waveform in FIG. 4, corresponds to the acoustic signal produced when substantially no radiation wave, that is, no radiation wave 24 of FIG. 1, is present in or about the plasma, for example, plasma 16 of FIG. 1. Waveform 62, that is, the red-dashed waveform in FIG. 4, corresponds to the acoustic signal produced when a THz wave of about 100 kV per cm, that is, radiation wave 24 of FIG. 1, is present in or about the plasma, for example, plasma 16 of FIG. 1. As shown in FIG. 4, especially in inset 66, in this aspect of the invention, the presence of the 100 kV per cm THz radiation enhances the amplitude of frequency domain waveform 64 compared to the amplitude of frequency domain waveform 62 with no such THz radiation present. The range of the percent enhancement shown in inset 66 is limited by the 140 kHz bandwidth of the microphone used to detect the acoustic signals. The relatively uniform enhancement shown in inset 66 of FIG. 4 suggests that the THz wave only increases the total acoustic pulse energy but has little or no effect on changing the spectral distribution. It is speculated that the reason for this might be that the THz wave heats electrons in such a short time period, for example, within 1-2 picoseconds (ps), that the THz wave heating, except producing a higher local plasma temperature, does not change the temporal evolution of shock wave and acoustic waves which are formed on the microsecond time scale.

According to aspects of the invention, the enhancement in the amplitude of the sound pressure due to the presence of the THz radiation over the sound pressure produced when no THz radiation is present at a given time may be at least about 5%, or at least about 10% or 15%, as shown in FIG. 4. Under appropriate conditions, it is conceived that the sound pressure in the frequency domain may be enhanced at least about 20%, and even at least about 25%, or higher, than when little or no radiation wave is present. Accordingly, in aspects of the invention, the methods and systems disclosed herein may be useful in detecting the presence of radiation waves, for example, THz radiation waves, by detecting enhancements or variations in the acoustic signal detected in the frequency domain, for example, by an acoustic signal detector.

Figure 5:
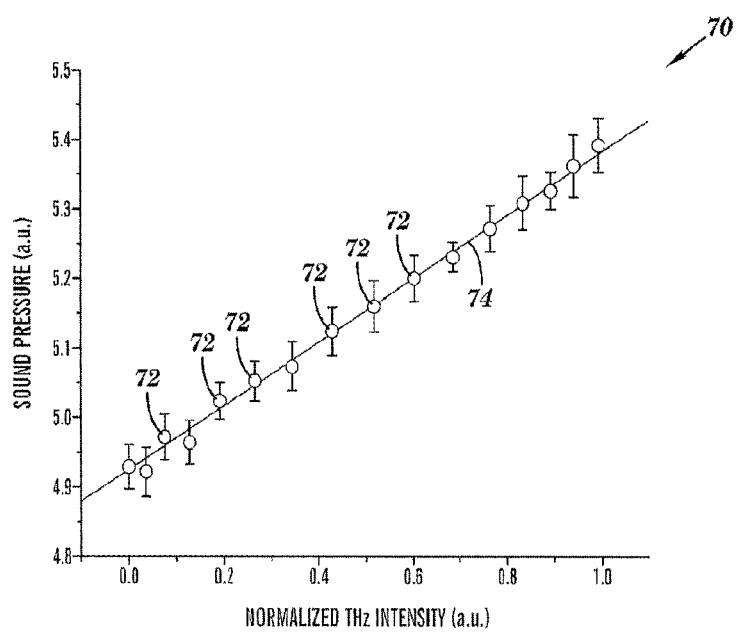
FIG. 5 is a graphical representation of the measured acoustic signal detected at a given frequency for different radiation wave intensities incident on a single-color laser-induced plasma and the linear fit of the measured acoustic signal according to one aspect of the invention.

FIG. 5 is a graphical representation 70 of the measured acoustic signal 72 detected at a discrete frequency of 100 kHz. A pair of wire grid polarizers was used to determine the acoustic enhancement dependence on THz intensity, specifically, normalized, varying THz radiation wave intensities, incident on a single-color laser-induced plasma. A lock-in amplifier measured the acoustic signal at 100 kHz, using the 100th harmonic of the laser repetition rate (1 kHz). FIG. 5 illustrates the acoustic enhancement at 100 kHz for different THz intensities. As shown, the good agreement between the measured acoustic signals 72 and the linear fit 74 indicates that enhanced acoustic pressure is linearly dependent on incident THz wave intensity according to one aspect of the invention.

As shown in FIGS. 4 and 5, according to aspects of the invention, the enhancement of acoustic emission, for example, the enhancement of acoustic waves 18 and 38 in FIGS. 1 and 2, respectively, may extend from audible frequency range, that is, 20 Hz to about 20 kHz, into the ultrasonic range, that is, typically greater than 20 kHz, and is a linear function of the intensity of the radiation wave, for example, the THz radiation wave intensity, incident upon the plasma. Accordingly, it is thus believed that the radiation-enhanced acoustic aspects of the present invention can be useful for radiation wave detection, for example, THz radiation wave detection.

In addition, in one aspect of the invention, by employing multi-color optical beams, for example, dual-color beam 32 shown in FIG. 2, to produce the plasma 36, spectroscopic information may also be encoded into the acoustic emission 38. For example, by using dual-color laser excitation to manipulate free electron drift it is possible to modulate the enhanced acoustic signal and recover coherent radiation time-domain waveforms, for example, coherent THz time-domain waveforms, by simply "listening" to the plasma. That is, the two-color aspect of the present invention provides for the detection of both amplitude and phase, that is, coherent detection. In contrast, single-color excitation is typically limited to incoherent detection, for example, where only the amplitude of the radiation wave can be detected. The detection of both the amplitude and the phase of the radiation wave, for example, the THz wave, permits aspects of the invention to be used for spectroscopy, among other applications. It is believed that the application of this invention to the field of spectroscopy for use in any field of science and technology is very promising. It is conceived that multi-color optical beams may make it possible to obtain temporal electric field profiles of the radiation waves 44, for example, THz radiation waves or pulses, by simply detecting the acoustic wave 38, that is, by "listening" to the plasma 36.

Figure 6:
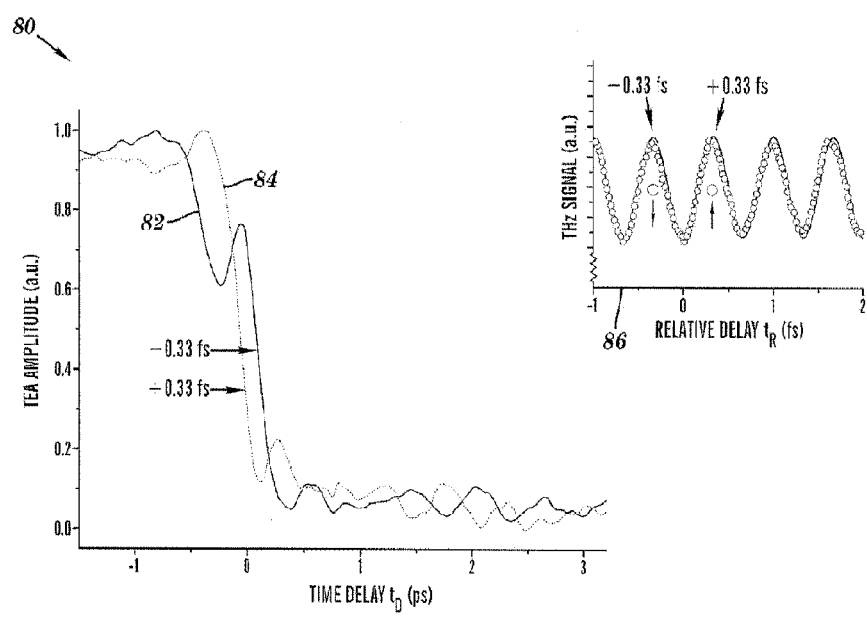
FIG. 6 is a graphical representation of the effect of the time delay upon the amplitude of the enhanced acoustic signal due to the presence of THz radiation.

FIG. 6 is a graphical representation 80 of the effect of the time delay, $t_D$, upon the amplitude of the enhanced acoustic signal due to the presence of THz radiation. In one aspect, this may be referred to as "THz-enhanced acoustics" or TEA. As shown in FIG. 6, the effect of aspects of the invention may be referred to as "TEA amplitude" in arbitrary units of measurement (that is, "a.u."). As noted above, the time delay, $t_D$, is the delay between the impact or presence of the optical beam(s) 12, in FIG. 1, or 32, in FIG. 2, and the impact or presence of the radiation wave 24 upon the portion of the volume of gas 14. The variation of the time delay $t_D$ shown in FIG. 6 is sometimes referred to as "scanning the time delay." The variation of the time delay $t_D$ can be provided by a scanning mechanical stage.

As shown in FIG. 6, when the THz pulse leads the optical pulse in time, that is, the time delay, $t_D$, is positive, there is no acoustic enhancement, because there is no interaction between the THz pulse and the plasma; however, when the field of the THz pulse begins to interact with the plasma, a sharp rise in the acoustic signal is observed, with the period of rising time comparable to the width of a single-cycle THz pulse. Following the rise shown in FIG. 6, a slow decay of the acoustic signal of the order of nanoseconds is observed and agrees with the temporal profile of the electron density decay due to electron-ion recombination.

The enhancement of the acoustic pressure illustrated in FIG. 6 is attributed to electron heating in the THz field and the subsequent increased temperature of air molecules through electron-molecule collision. Since the electron relaxation time, $\tau$, at atmospheric pressure is small in comparison to the THz pulse duration, the pressure enhancement $\Delta p$ can be approximated as $$\frac{e^2 \tau}{m_e} \int_{t_D}^{\infty} E_{THz}(t')^2 \, dt'$$

The quadratic dependence of the acoustic pressure enhancement from the THz field is also consistent with the linear fit 74 shown in FIG. 5.

Aspects of the present invention can also be used to coherently detect THz pulses using a dual-color, laser-produced plasma, for example, as shown in FIG. 2. By using the superposition of two optical pulses, for example, having wavelengths $\omega$ and $\Omega$ (for example, $\omega$ is about 800 nm and $\Omega$ is about 400 nm), linearly polarized in the same direction, the net electron drift inside the plasma can be controlled by changing the relative phase or time delay between the two optical pulses, $t_R$. The symmetry of drift velocity can be determined by the THz wave generation from laser-induced plasma and results are shown in the inset 86 in FIG. 6. The inset 86 shown in FIG. 6 is a graphical representation of measured THz wave generation from dual-color laser-induced plasma at varying time delay $t_R$ with no external THz radiation field present. The curves in inset 86 illustrate that the symmetry of drift velocity can be determined by the THz wave generation from laser-induced plasma. As shown in inset 86, the quasi-unipolar net drift is in the parallel direction at a phase of tR=+0.33 fs, while the quasi-unipolar net electron drift is in the anti-parallel direction at the phase of $t_R$=−0.33 fs. When a THz field is introduced for each of these relative optical phase delays between $\omega$ and $\Omega$, the electrons that experience the THz field are either slightly accelerated or slightly decelerated depending on whether the THz field is anti-parallel or parallel to the direction of the electron net drift. Scanning the delay between the THz and optical pulses $t_D$ for a given relative delay $t_R$ of −0.33 fs and +0.33 fs between the $\omega$ and $\Omega$ pulses, the rising enhancement curves 82 and 84 shown in FIG. 6 for opposite net electron drift directions are obtained.

The two curves 82 and 84 shown in FIG. 6 represent the TEA amplitude for two time delays $t_R$, that is, the time delay between the dual-color pulses of frequencies $\omega$ and $\Omega$ of the optical signal 32, as indicated in FIG. 2. For the data shown in FIG. 6, $\omega$ is about 800 nm and $\Omega$ is about 400 nm and the representative time delays $t_R$ are −0.33 fs and +0.33 fs. In FIG. 6, curve 82 corresponds to a $t_R$ of −0.33 fs and curve 84 corresponds to a $t_R$ of +0.33 fs. Curves 82 and 84 represent enhanced acoustic signals detected by a microphone positioned near a laser-induced plasma, for example, microphone 46 positioned near plasma 36 shown in FIG. 2.

According to aspects of the invention, under parallel and anti-parallel conditions, the free electrons in the plasma created by the THz pulses at frequencies $\omega$ and $\Omega$ will either be decelerated or accelerated along the direction of the THz field, contributing to the overall acoustic emission. By subtracting the TEA curves 82 and 84 for these respective phases, both "background" acoustic emission from the dual-color plasma and the second-order heating term, (that is, $\sim E_{THz}(t)^2$) are canceled, since these are symmetric for the dual-color ionization. This leaves only the change in acoustic emission from electron momentum change by the THz field before the first collision event (ETHz (t) first-order term), after which the electron drift is randomized. Therefore, $E_{THz}$ can be calculated by $$\Delta p(-0.33 \text{ fs}) - \Delta p(+0.33 \text{ fs}) \propto E_{THz}(t).$$

Figure 7:
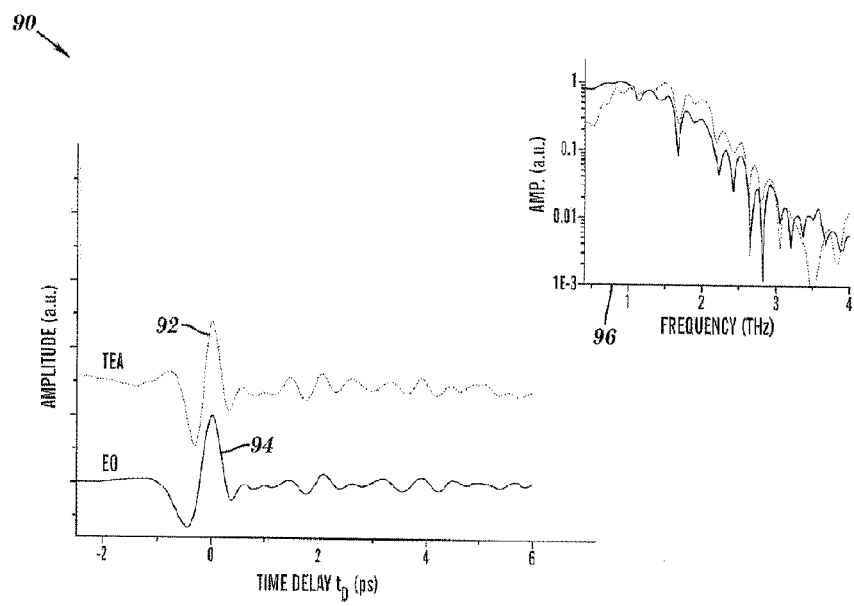
FIG. 7 is a graphical representation of a THz time-domain waveforms obtained using the THz-enhanced acoustics method compared with prior art electro-optic methods according to an aspect of the present invention.

According to aspects of the invention, it is also possible to recover the THz signal if, for one case, we used a phase delay of 0 fs between $\omega$ and $\Omega$ (for example, 2 $\omega$) that produces a symmetric electron drift, and in the other produces a case of asymmetry (parallel or anti-parallel). In the present investigation, parallel and anti-parallel delays were used because this provides a factor of 2 in the pressure contribution from the THz signal. To verify the equation above, the measured THz time-domain waveforms and spectra using this method are compared with conventional electro-optic (EO) sampling as shown in FIG. 7.

According to aspects of the invention, by subtracting the THz-enhanced acoustics (TEA) curves 82, 84 for two respective phases, for example, for $t_R=-0.33$ fs and $t_R=+0.33$ fs, the influence of the radiation field, for example, the THz radiation field, on the net electron drift and translational energy transfer of the plasma can be revealed in the form of, for example, a coherent THz time domain waveform. A comparison between THz waveforms acquired using THz-enhanced acoustics according to aspects of the invention and a traditional method using an electro-optic crystal is shown in FIG. 7. FIG. 7 is a graphical representation 90 of the THz time-domain waveforms obtained using the THz-enhanced acoustics method according to an aspect of the present invention, curve 92, and conventional electro-optical (EO) sampling, curve 94. The THz-enhanced acoustics waveform represented by curve 92 is obtained by subtraction of the curves 82 and 84 shown in FIG. 6. The inset 96 in FIG. 7 illustrates the corresponding THz radiation spectra. Clearly, aspects of the present invention represented by curve 92 are consistent with conventional methods represented by curve 94. From the data shown in FIG. 7 and the inset 96 in FIG. 7, it is apparent that aspects of the present invention produce similar results to conventional EO methods and the locations of water absorption lines are consistent with previously reported data.

Figure 8:
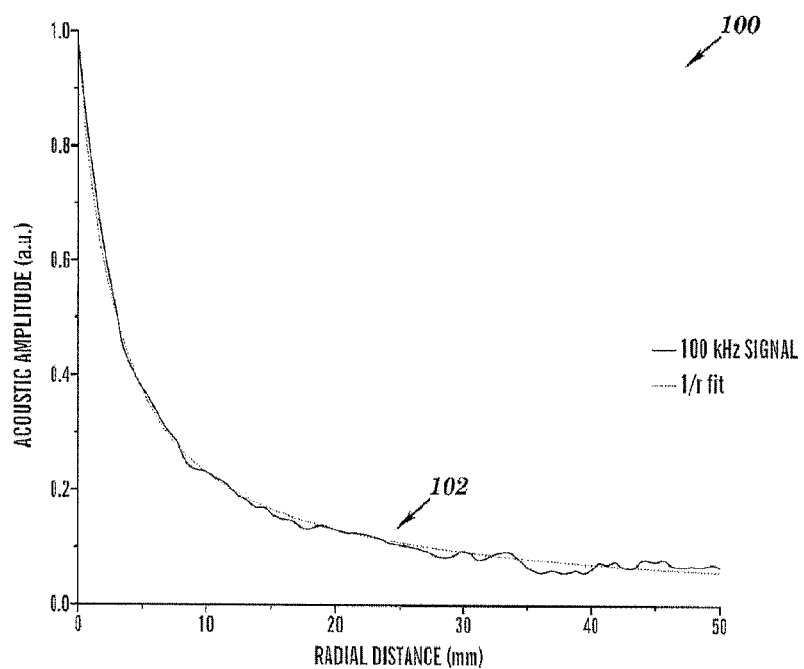
FIG. 8 is a graphical representation of a typical decay or attenuation curve of acoustic signal or sound pressure with radial distance from a plasma.

FIG. 8 is a graphical representation 100 of a typical decay or attenuation curve 102 of acoustic signal or sound pressure (that is, a "1/r decay") with radial distance from a plasma. The plasma and acoustic signal were generated by focusing a 1 kHz repetition rate single color laser into air and then detecting the 100 kHz acoustic component using a lock-in amplifier to lock to the 100th harmonic of the 1 kHz laser repetition frequency. The relatively low attenuation of the acoustic wave in ambient air shown in FIG. 8 makes it possible to use laser-induced plasma as a sensor to detect THz waves at standoff distance and transmit the information about the THz waves back via acoustic waves.

Figure 9:
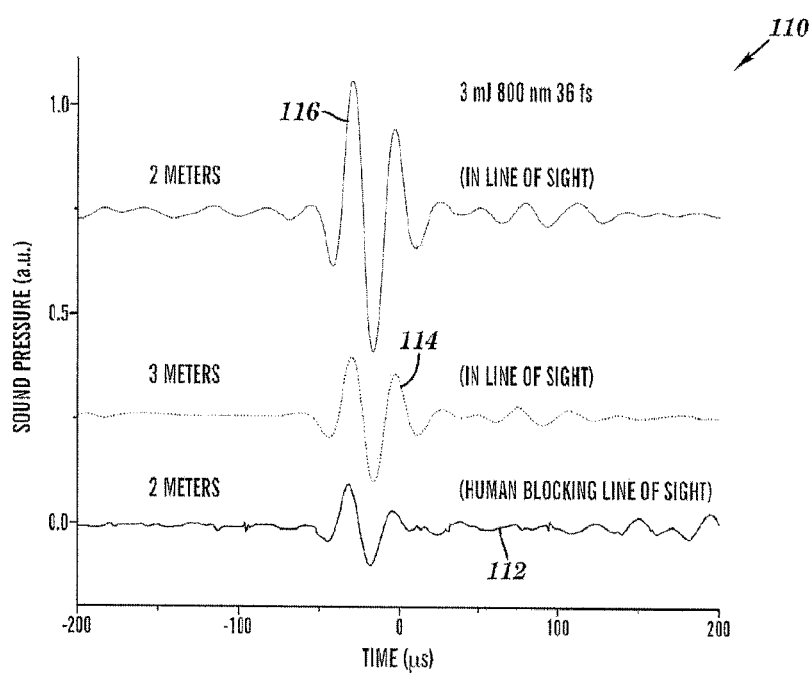
FIG. 9 is a graphical representation of various acoustic signals detected at various distances from a plasma source.

FIG. 9 is a graphical representation 110 of various acoustic signals detected at various distances from a plasma source. The acoustic signals in FIG. 9 were generated by a 3 millijoule, 800 nm, 36 fs laser pulse directed into a volume of air to create a plasma. Curve 112 represents the acoustic or sound wave detected by a microphone at about 2 meters from the plasma with a human being positioned between the plasma and the microphone. Curve 114 represents the acoustic or sound wave detected by a microphone at about 3 meters from the plasma with no obstructions between the plasma and the microphone, that is, the microphone was within the line of sight of the plasma. Curve 116 represents the acoustic or sound wave detected by a microphone at about 2 meters from the plasma with no obstructions between the plasma and the microphone, that is, again, the microphone was within the line of sight of the plasma. Curves 114 and 116 clearly indicate the attenuation of the acoustic signal with distance from the plasma source. However, curves 112 and 116 also clearly indicate that, even when obstructed, an acoustic signal can be detected at a remote position from the plasma. The curves in FIG. 9 clearly demonstrate the feasibility for detection of radiation-enhanced acoustic waves at various distances and positions, even at positions without a direct line of sight to the plasma being "listened to." The curves in FIG. 9 indicate that, according to aspects of the invention, a realistic solution for coherent remote radiation wave, for example, THz wave, detection is provided. In the testing of aspects of the invention that resulted in the curves shown in FIG. 9, the detection was performed without the use of any acoustic collection enhancing devices, for example, parabolic reflectors. The use of one or more acoustic collection enhancing devices can dramatically increase the quality of the signal collected. For example, aspects of the invention using a parabolic reflector yielded waveforms similar to those shown in FIG. 9, but were detected at distances up to 11 meters (that is about, 36 feet away).

Figure 10:
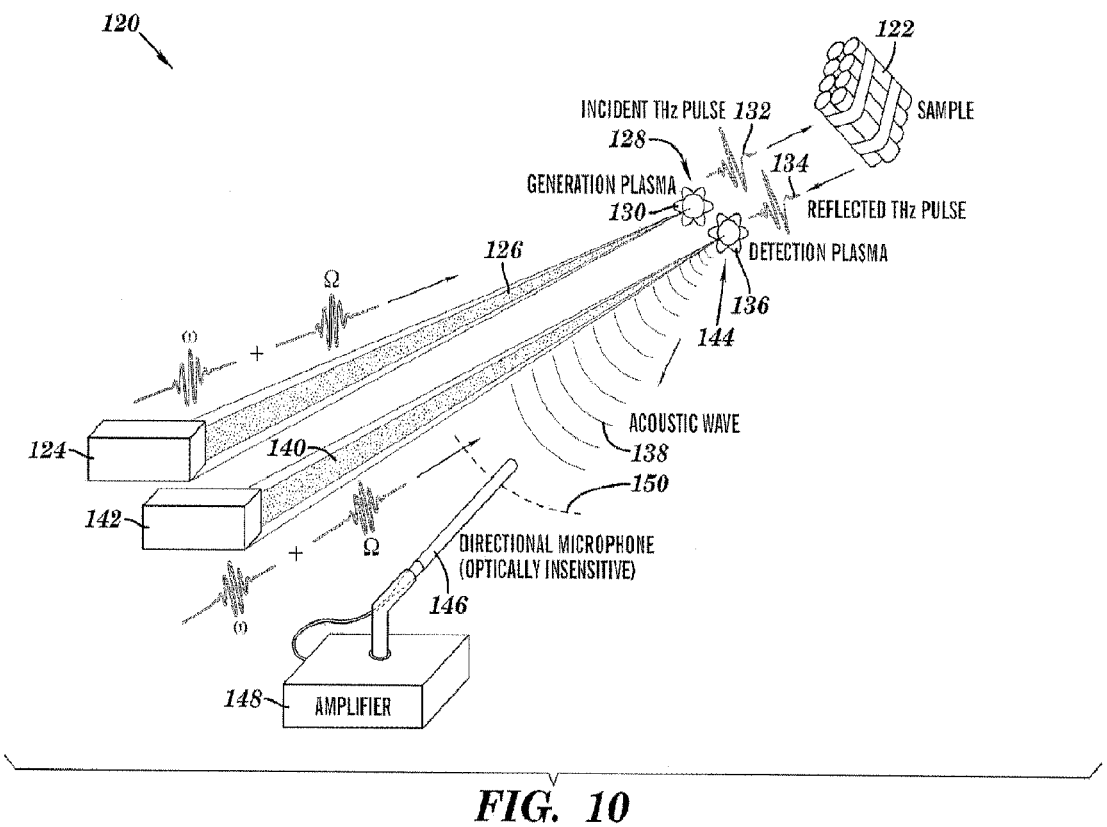
FIG. 10 is a schematic diagram of a remote spectroscopy system according to one aspect of the invention.

FIG. 10 is a schematic diagram of a remote spectroscopy system 120 according to one aspect of the invention. As shown in FIG. 10, system 120 may be used to detect a target 122, for example, a material harmful to humans, such as, an explosive, a biological agent, a chemical agent, or a vapor emitted from one of these agents. However, in one aspect, target 122 may be any material that may be desired to be detected, for example, an innocuous chemical or substance, for example, to remotely determine the material composition of a substance or structure. According to one aspect, system 120 includes a source of optical beam 124, for example, a first source, to provide an optical beam 126, for example, a first optical beam, directed toward a volume of gas 128, for example, air. Optical beam 126 may be similar to and have all the attributes of optical beam 12 or 32 discussed above. Source 124 may also include means or be adapted to direct or focus optical beam on the volume of gas 128, such as, radiation refracting lenses or radiation deflecting mirrors and the like. As discussed above, optical beam 126 is typically a laser beam or a laser pulse, for example, a femtosecond laser pulse, adapted to ionize at least a portion of volume of gas 128 to generate a plasma 130, for example, a first or "generation plasma," and THz radiation or THz pulse 132. When THz radiation is generated by focusing a laser beam (for example, a two-color laser beam) into air, the resulting THZ radiation is typically highly directional and forward propagating. For example, the divergence angle of the generated pulse may be dependent upon the effective focal length of the focusing optic. A representative THz radiation pulse 132 directed toward target 122 is shown in FIG. 10. As is known in the art, interaction or reflection of incident THz radiation 132 to produce a reflected THz radiation or THz pulse 134. As is also known in the art, due to the interaction or reflection of THz radiation 132 with target 122, reflected THz radiation 134 (or radiation incident on plasma 136) contains at least some characteristic indicative of the target 122, for example, at least one characteristic that can be detected from radiation 134 whereby a characteristic or the nature of target 122 can be determined. For example, in one aspect, a characteristic of reflected THz radiation 134 may be compared with documented characteristics of THz radiation reflected or interacting with a library of materials to determine the nature of target 122. In contrast to prior art methods, such as, those employing plasma fluorescence as the detector (which may be easily saturated by a bright broadband light source such as the sun), aspects of the present invention may be substantially optically insensitive to the presence of solar radiation, that is, sun light.

According to an aspect of the present invention, a second or detector plasma 136 may be provided to interact with reflected THz radiation 134 (or radiation incident on plasma 136), and, according to an aspect of the invention, generate an acoustic signal 138 that can be detected and analyzed to determine at least one characteristic of reflected THz radiation 134 and/or at least one characteristic of target 122. Detector plasma 136 may typically be generated by an optical beam 140, for example, a second optical beam, from a second source 142, for example, a second source directed toward a volume of gas 144, for example, air, in the proximity of reflected THz wave 134. Again, optical beam 140 is adapted to ionize at least a portion of the volume of gas 144 to create plasma 136, for example, a detection plasma.

According to aspects of the invention, the acoustic signal 138 created by the interaction of the reflected THz radiation 134 and the detector plasma 136 is detected by an acoustic wave detector, for example, microphone 146 shown in FIG. 10, for instance, a G.R.A.S. 40DP or 40AC microphone, or its equivalent. The detected signal can be manipulated, for example, amplified, and/or processed by appropriate receiver/processor 148 operatively connected to microphone 146, for example, to produce an output similar to the curves shown in any one or more of FIGS. 3 through 9.

As shown in FIG. 10, optical beams 126 and 140 may be multi-color optical beams, for example, have two or more frequencies, for example, frequencies ω and Ω shown in FIG. 10. However, in one aspect, optical beams 126 and 140 may be single color or multi-color beams, for example, dual-color beams. For example, in one aspect, optical beam 126 may be single-color and optical beam 140 may be dual-color. In one aspect, a dual-color beam may comprise a first frequency ω and a second frequency Ω, for example, a harmonic of first frequency ω, for example, Ω may be about half the wavelength of frequency ω or about twice the frequency of ω. (Again, since frequencies ω and Ω are expressed as wavelengths, half of the frequency ω corresponds to twice wavelength of ω.) In one aspect, ω may be about 800 nm and Ω may be 400 nm. As noted above, beams 126 and 140 may comprise pulses of multiple frequencies separated by a time delay $t_R$.

In one aspect, an acoustic signal enhancing or concentrating device may be used to enhance the acoustic signal 138 to enhance sound collection efficiency prior to reception and/or detection by microphone 146. For example, in one aspect, a wave guide (not shown) or a dish-shaped collector 150 (shown schematically in phantom in FIG. 10) may be provided about microphone 146 to enhance the amplitude of the acoustic signal 138 received by microphone 146. (When using a parabolic reflector, typically, a microphone 146 is placed pointing into collector 150, and not as schematically shown in FIG. 10.). In one aspect, an acoustic reflector, for example, a parabolic reflector may be mounted about microphone 146, for example, where microphone 146 may be positioned at or about the focus of the parabolic reflector, to enhance the acoustic signal 138 received by microphone 146. In another aspect, a wave guide or channel may be positioned between plasma 136 and microphone 146 to enhance reception of the acoustic signal 138 by microphone 146. The use of a wave guide or collector may be particularly effective for remote detection where the attenuation of the acoustic wave signal I may be more pronounced.

Additional aspects and features of the invention are disclosed in the following papers:

"Laser-induced photoacoustics influenced by single-cycle terahertz radiation," by Clough, et al., *Optics Letters*, Vol. 35, No. 21, Nov. 1, 2010;

"Enhancement of photoacoustic emission through terahertz-field-driven electron motions," by Liu, et al., *Physical Review*, E 82, 066602 2010, Dec. 13, 2010; and "Encoding terahertz signatures into laser-induced plasma acoustic waves," by Clough, et al., Proc. of SPIE, Vol. 7938, 793804, pending publication, the disclosures of which are incorporated by reference herein in their entirety.

Aspects of the present invention provide systems and methods for detecting and/or measuring of acoustic waves, in particular, THz enhanced acoustic (TEA) waves from a laser-induced plasma, for example, under single-cycle THz radiation. The TEA emission may vary linearly with the THz wave intensity incident on the plasma, and at least 5% and 10% acoustic enhancement can be provided. Two-color laser fields can be used to coherently manipulate the electron drift velocity and control the TEA emission. Measuring the acoustic pressures at opposite electron drift velocities provides the information of the coherent THz time-domain waveform. The coherent THz wave detection using acoustic pressure enhancement is a promising technique for the remote THz sensing because it is free of the strong water vapor attenuation and is not limited by the directionality of signal collection. Aspects of the invention can be used for coherent THz wave detection, for example, at remote distances, and as a diagnostic tool for dynamic plasma interactions, for example, with electromagnetic radiation. As will be appreciated by those skilled in the art, features, characteristics, and/or advantages of the various aspects described herein, may be applied and/or extended to any embodiment (for example, applied and/or extended to any portion thereof).

Although several aspects of the present invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

We claim:

1. A method of detecting a target, the method comprising:
directing a first optical beam into a first volume of gas;
ionizing at least a portion of the first volume of gas with the first optical beam to produce an emitter plasma and to emit terahertz radiation directed toward a target;
directing a second optical beam into a second volume of gas;
ionizing at least a portion of the second volume of gas with the second optical beam to produce a sensor plasma; and
detecting an acoustic signal produced from an interaction of an incident terahertz wave with the sensor plasma, the incident terahertz wave produced by an interaction of the terahertz radiation with the target.

2. The method as recited in claim 1, further comprising focusing the incident terahertz wave in the sensor plasma.

3. The method as recited in claim 1, wherein the target comprises a remote target.

4. The method as recited in claim 1 wherein detecting comprises focusing the acoustic signal from the interaction of the incident terahertz wave and the sensor plasma.

5. The method as recited in claim 1, wherein the target comprises a substance harmful to humans.

6. The method as recited in claim 1, wherein the detecting is performed more than 10 meters from the target.

7. The method as recited in claim 1, wherein the first volume and the second volume at least partially overlap.

8. The method as recited in claim 1, further comprising processing the acoustic signal detected with spectroscopic analysis.

9. The method as recited in claim 1, wherein at least one of the first optical beam and the second optical beam comprises a dual-color laser pulse comprising a first pulse at a first frequency and a second pulse at a second frequency different from the first frequency, and wherein the first pulse and the second pulse are temporally separated by a time delay.

10. The method as recited in claim 9, further comprises varying the time delay.

* * * * *